United States Patent [19]
Hoegnelid

[11] Patent Number: 5,309,096
[45] Date of Patent: May 3, 1994

[54] MAGNETIC FIELD DETECTOR FOR A MEDICAL DEVICE IMPLANTABLE IN THE BODY OF A PATIENT

[75] Inventor: Kurt Hoegnelid, Vaesterhaninge, Sweden

[73] Assignee: Siemens Aktiengesellschaft, Munich, Fed. Rep. of Germany

[21] Appl. No.: 933,736

[22] Filed: Aug. 24, 1992

[30] Foreign Application Priority Data

Aug. 26, 1991 [EP] European Pat. Off. ........ 91114252.9

[51] Int. Cl.$^5$ .................. G01R 33/02; G01R 33/028; A61N 1/08; A61N 1/37
[52] U.S. Cl. .............................. 324/256; 73/DIG. 4; 324/226; 324/260; 607/19
[58] Field of Search ...................... 324/207.13, 207.22, 324/226, 223, 235, 244, 256-260; 73/DIG. 4; 340/573; 128/419 R, 420 R, 419 P, 419 PG, 419 D

[56] References Cited

U.S. PATENT DOCUMENTS

| | | |
|---|---|---|
| 3,865,119 | 2/1975 | Svensson et al. . |
| 4,186,324 | 1/1980 | Hartzell, Jr. . |
| 4,428,378 | 1/1984 | Anderson et al. . |
| 4,677,378 | 6/1987 | Tokura et al. ............... 324/207.13 |
| 4,866,383 | 9/1989 | Taliaferro ...................... 324/226 X |
| 4,887,032 | 12/1989 | Hetrick ......................... 324/260 X |

FOREIGN PATENT DOCUMENTS

| | | |
|---|---|---|
| 0191404 | 8/1986 | European Pat. Off. . |
| 0312605 | 4/1989 | European Pat. Off. . |
| 0431437 | 6/1991 | European Pat. Off. . |
| 2070937 | 9/1981 | United Kingdom . |

OTHER PUBLICATIONS

"A Vibrating Cantiliver Magnetic-Field Sensor," Hetrick, Sensors and Actuators, vol. 16, No. 3, Mar., 1989, pp. 197-207.

Primary Examiner—Gerard R. Strecker
Attorney, Agent, or Firm—Hill, Steadman & Simpson

[57] ABSTRACT

In a known magnetic field detector, an electrical coil (8) is secured to a motion-sensitive, for example piezoelectric sensor (3); this electrical coil is charged with an electrical current for detecting the magnetic field with the sensor (3) and an evaluation means (14) which follows thereupon. In order to also be able to employ the magnetic field detector given arrangement thereof in an implantable medical device as activity sensor for the physical activity of a patient, the current charging of the coil (8) can be switched on and off with a control signal (21), whereby the control signal (21) is utilized for characterizing the sensor signal as an activity signal corresponding to the physical activity or as a detection signal that detects a magnetic field.

7 Claims, 1 Drawing Sheet

MAGNETIC FIELD DETECTOR FOR A MEDICAL DEVICE IMPLANTABLE IN THE BODY OF A PATIENT

BACKGROUND OF THE INVENTION

1. Field of the Invention

The present invention is directed to a magnetic field detector for a medical device implantable in the body of a patient, having a motion-sensitive sensor to which an evaluation unit for the sensor signal is connected, an electrical coil that is secured to the sensor, and a current source that is connected to the coil and charges the coil with an electrical current for detecting a magnetic field in combination with the sensor and the evaluation unit.

2. Description of the Prior Art

A magnetic field detector disclosed in German OS 2 217 400 is composed of a magnetic switch or reed relay that is arranged in a heart pacemaker. The magnetic switch is closed by applying a magnet to the skin of the patient in whom the heart pacemaker is implanted, as a result of which a circuit in the heart pacemaker for defining the stimulation threshold of the heart is activated.

As long as only test functions of the implanted device such as, for example, identifying the stimulation threshold or a battery test, are to be triggered with the assistance of the external magnet, magnetic switches in the form of a reed relays have proven adequately reliable. Far higher demands are made on the reliability and response precision of the magnetic field detector if used to trigger (initiate) a treatment process, for example a stimulation pulse, defibrillation shock or the output of a medication dose, administered by the implanted device, or if it is used to inhibit such a treatment process that is automatically started on the basis of measured parameters of the device.

A general purpose magnetic field detector is disclosed in U.S. Pat. No. 4,887,032 wherein an electrical coil that is charged with alternating current by a current source is secured on a motion-sensitive piezoelectrical sensor. The frequency of the alternating current is matched to the resonant frequency of the sensor, so that the sensor is placed in a resonant oscillation given the presence of a magnetic field, whereby the output signal of the sensor is utilized in an evaluation unit for detecting the magnetic field.

It is an object of the present invention to optimize a known magnetic field detector of the type described immediately above for employment thereof in a medical device implantable in the body of a patient.

This object is achieved in accordance with the principles of the present invention in a magnetic field detector having the basic components of the detector of U.S. Pat. No. 4,887,032, but specially designed for implanted medical use. To this end, the current source in the magnetic field detector is connected to a novel control unit that generates a control signal for switching the current source on and off at prescribed points in time. The control signal is supplied to an evaluation unit which includes means for modifying the sensor signal with the control signal in such a way that the control signal defines the sensor signal as a detection signal for a magnetic field when the current source is switched on and defines the sensor signal as an activity signal corresponding to the physical activity of the patient when the current source is switched off.

A motion-sensitive (i.e., force-sensitive) activity sensor having evaluation circuitry for controlling the activity of a heart pacemaker is known from, for example, U.S. Pat. No. 4,428,378; however, a magnetic field detector and an activity sensor united in a single component have heretofore been unknown so that the space required in an implantable medical device employing the invention for realizing these two different sensor functions is minimized. When the current source for charging the coil with current is switched off, the sensor signal is defined by the control signal of the control unit as the activity signal corresponding to the physical activity of the patient. When the current source is switched on, by contrast, the sensor signal is indicated as the detection signal for a magnetic field.

The motion-sensitive (i.e., force-sensitive) sensor in the magnetic field detector of the invention is preferably a piezocrystal that is distinguished by a small structural size and by a high output signal.

It is necessary to be able to reliably distinguish the signal part of the sensor signal dependent on a magnetic field, that is generated by the magnetic field detector of the invention given the presence of an external magnetic field with the current charging the coil switched on, from the activity-dependent signal parts. For this purpose, it is possible to provide a defined curve or course for the current through the coil which is then embodied in the sensor signal. An individual electrical current pulse has thereby proven advantageous because the sensor signal thereby generated in the presence of an external magnetic field characteristically differs from the signals produced by mechanical impact stresses. The control signal of the control arrangement thereby defines the sensor signal as a detection signal for a magnetic field during a prescribed time interval that proceeds beyond the end of the current pulse, so that reverberations, caused by ringing of the sensor, that immediately follow the current pulse are not misinterpreted as activity of the patient. Moreover, the power consumption is especially low given the use of a single current pulse.

In this context, the evaluation unit of the magnetic field detector of the invention preferably contains a frequency discriminator and a threshold detector for monitoring the sensor signal for upward transgression of a prescribed signal threshold at a frequency corresponding to the natural frequency of the sensor. As a consequence of the individual current pulse which is supplied to the sensor given the presence of a magnetic field the motion-sensitive sensor behaves as if mechanically excited by an individual, brief mechanical impulse and then seeks to settle unimpeded with its natural frequency. The sensor signal corresponding thereto is a decaying oscillation with the natural frequency of the sensor, and thus clearly differs from other noise signals.

The reliability of the magnetic field detection can also be increased in an advantageous way by activating the frequency discriminator during the prescribed time interval when the coil is charged with the electrical current, so that the detection of a magnetic field is chronologically limited to the duration of the time interval.

For evaluating the activity signal, a signal processing circuit for the activity signal is preferably connected to the sensor, this signal processing circuit being inhibited when the coil is charged with the electrical current during the prescribed chronological duration.

DESCRIPTION OF THE PREFERRED EMBODIMENTS

Figure 1:
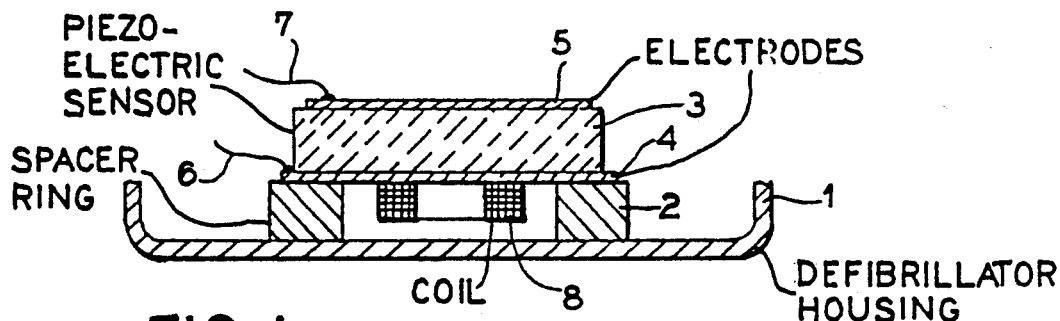
FIG. 1 is a side-sectional view of an exemplary embodiment of a motion-sensitive sensor with a coil secured thereto for use in the magnetic field detector of the invention.

In a schematic illustration, FIG. 1 shows a section through a part of the housing 1 of an implantable defibrillator or some other implantable medical device. A spacer ring 2 is glued on the inside wall of the housing 1, and a disc-shaped piezoelectrical sensor 3 provided with respective contact electrodes 4 and 5 at both sides is glued on this spacer ring 2. The contact electrodes 4 and 5 are respectively connected to terminals 6 and 7 across which the electrical voltage generated in the piezoelectric sensor 3 can be tapped. If the spacer ring 2 and the housing 1 each consist of an electrically conductive material, the voltage can also be tapped between the contact electrode 5 and the housing 1. An electrical coil 8 is arranged in the cavity that is formed by the contact electrode 4, the housing 1 and the inside of the spacer ring 2. This electrical coil 8 is firmly connected to the piezoelectric sensor 3 by being glued on the contact electrode 4. The electrical coil 8 can alternatively be connected to the piezoelectric sensor 3 at the opposite side thereof in the same way. In the illustrated exemplary embodiment, the electrical coil 8 is a wire coil; however, it is alternatively possible to form one or both of the contact electrodes 4 and 5 in the shape of helical interconnects which thus form the electrical coil.

Figure 2:
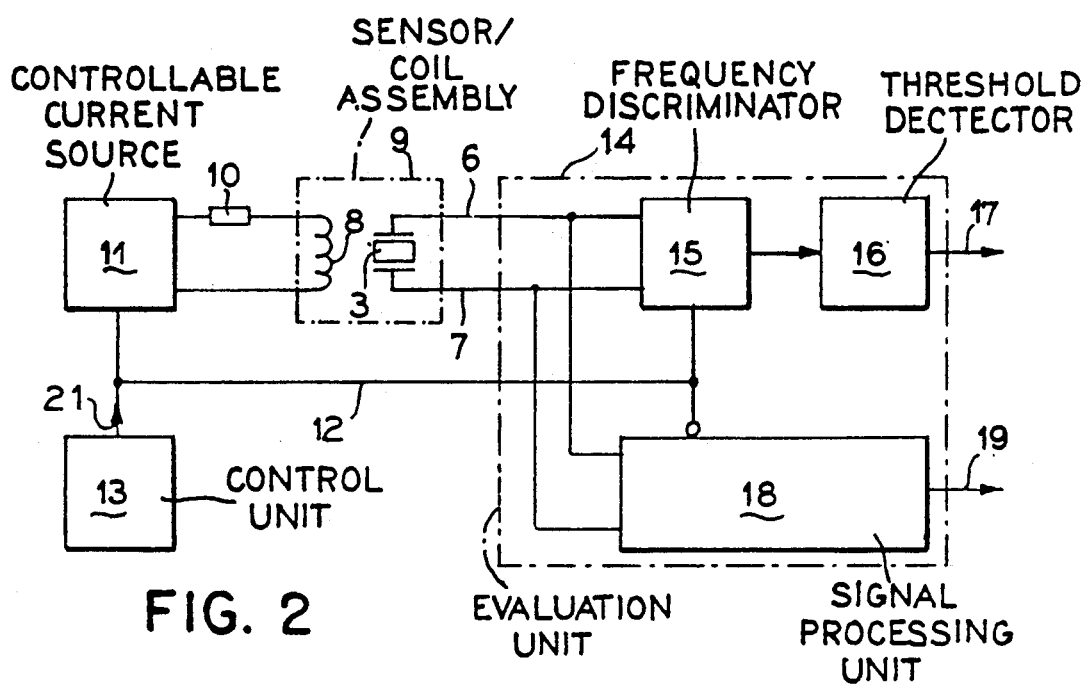
FIG. 2 is a block circuit diagram of the magnetic field detector of the invention.

FIG. 2 shows a simplified block circuit diagram of a circuit for a magnetic field detector in accordance with the invention. The dot-dashed boundary 9 thereby indicates that the electrical coil 8 and the piezoelectric sensor 3 are rigidly connected to one another in a sensor/coil assembly. The coil 8 is connected to a controllable current source 11 via a resistor 10. The current source 11 is connected via a control line 12 to a control unit 13 that activates the current source 11 to generate an output of a square-wave current pulse at prescribed, preferably programmable, time intervals. An evaluation unit 14 is connected to the sensor 3, with a frequency discriminator 15, set to the natural frequency of the piezoelectric sensor 3, having its input side in the evaluation unit 14 connected to the terminals 6 and 7 of the sensor 3. The frequency discriminator 15 is activated simultaneously with the activation of the current source 11 for the duration of a prescribed time interval. The frequency discriminator 15 is followed by a threshold detector 16 that has an output 17. As shall be described in greater detail below with reference to FIG. 3, a sensor signal that causes the evaluation means 14 to generate an output signal at its output 17 is generated in the piezoelectric sensor 3 as a consequence of the current pulse generated by the current source 11 given the presence of an external magnetic field.

A signal processing unit 18 for acquiring sensor signals that correspond to the physical activity of a patient in whom the device is implanted is also connected to the terminals 6 and 7 of the piezoelectric sensor 3. The signal processing unit 18 has an output 19 and is inhibited via the control line 12 by the control unit 13 for the duration of the prescribed time interval during which the evaluation unit 14 is activated.

Figure 3:
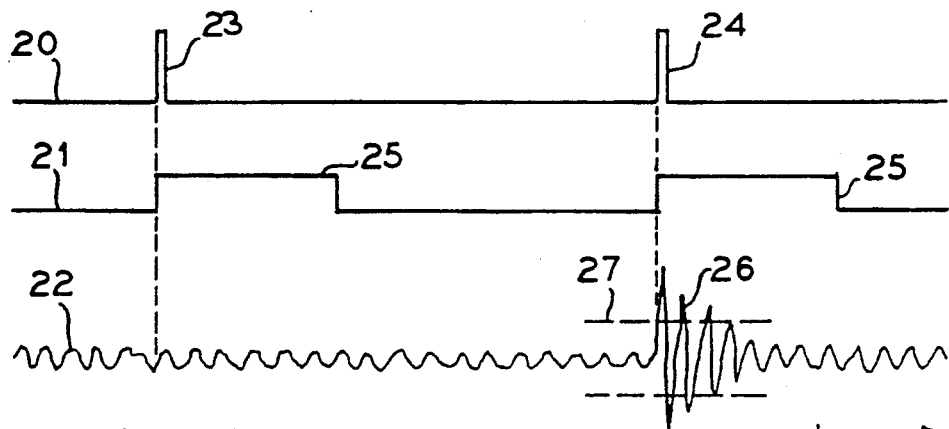
FIG. 3 shows examples for the current through the coil and the sensor voltage resulting therefrom given the lack of, and given the presence of, an external magnetic field.

In FIG. 3, the current through the coil 8 is referenced 20, the control signal generated by the control unit 13 via the control line 12 is referenced 21, and the sensor signal of the piezoelectric sensor 3 is referenced 22. As curve 20 shows, the current source 11 is driven by the control unit 13 to generate current pulses 23, 24 at regular time intervals of, for example, 1 second. Simultaneously with the generation of the current pulses 23, 24, the frequency discriminator 15 is activated by the control signal 21 for the duration of a time interval 25 and the signal processing unit 18 is simultaneously inhibited for the same duration. When, as in the case of the current pulse referenced 23, no external magnetic field is present, the piezoelectric sensor 3 remains uninfluenced by the current pulse 23 and generates a sensor signal at its two terminals 6 and 7 that corresponds to the momentary physical activity of the patient. This sensor signal 22 is processed by the signal processing unit 18 outside the time intervals 25 in such a way as is known, for example, from the aforementioned U.S. Pat. No. 4,428,378.

Let it be assumed in the case of the current pulse referenced 24 that an external magnetic field is present, so that a force is exerted on the coil 8 by the external magnetic field and by means of the magnetic field generated by the current in the coil 8, this force is transmitted to the piezoelectric sensor 3 connected thereto which generates a characteristic sensor signal 26. In the case of the square-wave current pulse 24, an impulse acts on the piezoelectric sensor 3 that excites the sensor 3 to generate an attenuated oscillation having the natural frequency of the sensor 3. The sensor signal 26 is monitored for this predetermined natural frequency in the frequency discriminator 15, and the threshold detector 16 generates an output signal when the oscillation having the natural frequency upwardly exceeds a prescribed threshold 27.

Although modifications and changes may be suggested by those skilled in the art, it is the intention of the inventor to embody within the patent warranted hereon all changes and modifications as reasonably and properly come within the scope of his contribution to the art.

I claim as my invention:

1. A magnetic field detector for a medical device implantable in the body of a patient, comprising:

a housing having a shape and size for implantation in the body of a patient;

a force-sensitive sensor, which generates a sensor signal, and an electric coil mechanically attached together and mounted as a unitary assembly in said housing;

current source means for supplying current to said coil so that a force is exerted on said coil in the presence of a magnetic field, said force being transmitted to said sensor;

control means for generating a control signal for switching said current source means on and off at prescribed points in time and thereby modifying said sensor signal for defining said sensor signal as a detection signal for a magnetic field when said current source means is switched on and for defining said sensor signal as an activity signal corresponding to the physical activity of said patient when said current source means is switched off; and evaluation means, activated by said control signal, for evaluating said sensor signal dependent on whether said sensor signal is defined as a detection signal for a magnetic field or as an activity signal.

2. A magnetic field detector as claimed in claim 1 wherein said motion-sensitive sensor is a piezoelectric sensor.

3. A magnetic field detector as claimed in claim 1 wherein said current source means is a means for generating an electrical current pulse when switched on by said control means, and wherein said control signal supplied to said evaluation means defines said sensor signal in said evaluation means as a detection signal for a magnetic field during a prescribed time interval following the end of said current pulse.

4. A magnetic field detector as claimed in claim 3 wherein said evaluation means includes a frequency discriminator, to which said sensor signal is supplied, and a threshold detector comprising, in combination, a means for monitoring said sensor signal for an upward transgression of a prescribed signal threshold at a frequency corresponding to the natural frequency of said sensor.

5. A magnetic field detector as claimed in claim 4 wherein said frequency discriminator is supplied with said control signal and is enabled by said control signal during said prescribed time interval.

6. A magnetic field detector as claimed in claim 3 wherein said evaluation means includes means for processing said sensor signal defined as an activity signal, said means for processing being connected to said sensor and receiving said control signal, said control signal inhibiting said means for processing during said prescribed time interval.

7. A magnetic field detector for a medical device implantable in the body of a patient, comprising:

a housing having a size and shape for implantation in the body of a patient;

a motion-sensitive sensor, which generates a sensor signal, and an electrical coil mechanically connected together forming a unitary assembly disposed in said housing;

current source means connected to said coil for charging said coil with a current pulse when said current source means is switched on;

control means for generating a control signal supplied to said current source means for switching said current source means on and off at prescribed points in time for thereby defining said sensor signal as a detection signal for a magnetic field when said current source is switched on and for a prescribed time interval immediately following said current pulse and for, except for said prescribed time, defining said sensor signal as an activity signal corresponding to the physical activity of said patient when said current source is switched off;

a frequency discriminator supplied with said sensor signal and with said control signal so that said frequency discriminator is enabled during said prescribed time interval;

a threshold detector following said frequency discriminator, said threshold detector and said frequency discriminator forming, in combination, means for monitoring said sensor signal for upward transgression of a prescribed signal threshold at a frequency corresponding to the natural frequency of said sensor during said prescribed time interval; and signal processing means supplied with said sensor signal and with said control signal, for analyzing said sensor signal when said sensor signal is defined as an activity signal, said signal processing means being inhibited by said control signal during said prescribed time interval.

* * * * *